United States Patent [19]

Tashiro

[11] Patent Number: 4,871,229
[45] Date of Patent: Oct. 3, 1989

[54] METHOD FOR ASSEMBLING OPTICAL FIBER BUNDLES IN AN ENDOSCOPE

[75] Inventor: Yoshio Tashiro, Hachioji, Japan

[73] Assignee: Olympus Optical Co., Ltd., Tokyo, Japan

[21] Appl. No.: 267,503

[22] Filed: Nov. 4, 1988

[30] Foreign Application Priority Data

Nov. 11, 1987 [JP] Japan .................. 62-282966

[51] Int. Cl.$^4$ ............................................. A61B 1/06
[52] U.S. Cl. ................... 350/96.26; 128/6; 29/458; 350/320
[58] Field of Search ............... 350/96.24, 96.25, 96.26; 128/4, 5, 6; 29/433, 434, 458

[56] References Cited

U.S. PATENT DOCUMENTS

| | | | |
|---|---|---|---|
| 4,267,828 | 5/1981 | Matsuo | 350/96.26 X |
| 4,341,205 | 7/1982 | Hosono et al. | 350/96.26 X |
| 4,396,247 | 8/1983 | Simon et al. | 29/458 X |
| 4,400,863 | 8/1983 | Schroeder | 29/458 X |
| 4,592,574 | 6/1986 | Vollmuth et al. | 29/434 X |
| 4,690,499 | 9/1987 | Taylor et al. | 350/320 X |
| 4,736,734 | 4/1988 | Matsuura et al. | 350/96.26 X |
| 4,788,967 | 12/1988 | Ueda | 350/96.26 X |
| 4,813,400 | 3/1989 | Washizuka et al. | 350/96.26 X |

FOREIGN PATENT DOCUMENTS 61-245120 9/1986 Japan .

Primary Examiner—William L. Sikes
Assistant Examiner—Akm E. Ullah
Attorney, Agent, or Firm—Ladas & Parry

[57] ABSTRACT

A method for assembling optical fiber bundles in an endoscope, comprising an insertion step of passing at least one optical fiber bundle through a flexible tube constituting an insertion section of the endoscope, a fitting step of fitting a reinforcement pipe member on an end portion of the optical fiber bundle passed through the flexible tube, and a coupling step of coupling the opposite end portions of the optical fiber bundle, on which the reinforcement pipe member is fitted, individually to a control section and a distal end member of the endoscope.

10 Claims, 4 Drawing Sheets

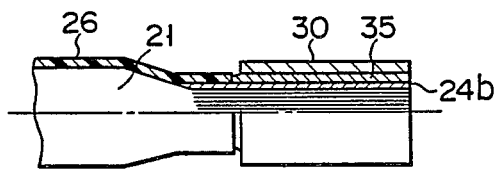
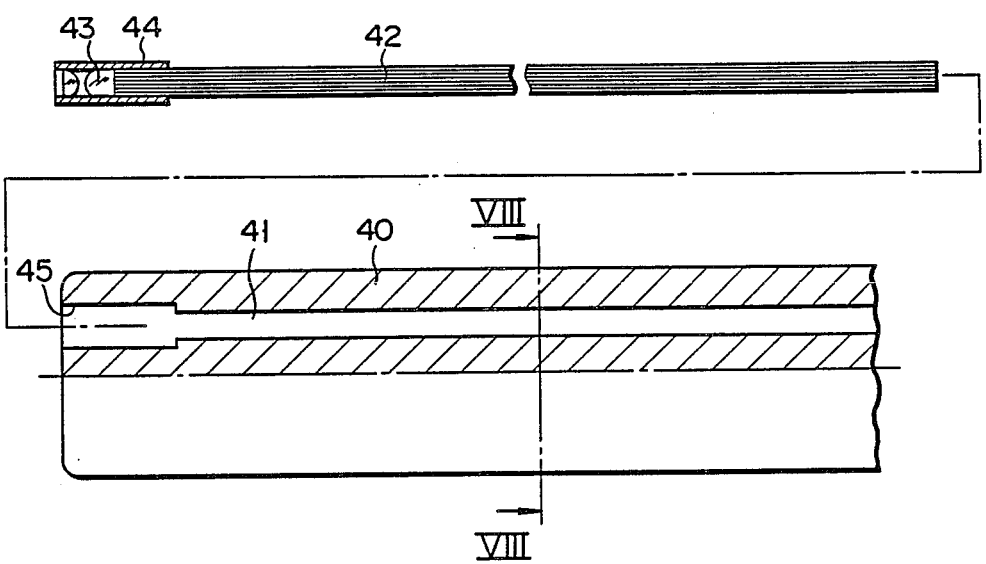
FIG. 6
FIG. 7
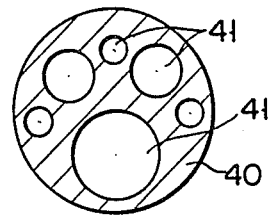
FIG. 8

METHOD FOR ASSEMBLING OPTICAL FIBER BUNDLES IN AN ENDOSCOPE

BACKGROUND OF THE INVENTION

1. Field of the Invention

The present invention relates to an endoscope, and more particularly, to an assembling method for coupling optical fiber bundles of an endoscope, such as an image guide and a light guide, to a distal end member and a control section.

2. Description of the Related Art

In a typical conventional endoscope, optical fiber bundles, such as an image guide and a light guide, are passed between a control section and a distal end member of an insertion section, which, extending from the control section, is adapted to be inserted into the body cavity or the like. The image guide is optically coupled to an eyepiece portion at the control section and an objective lens mounted on the distal end member. The light guide optically connects a light source connector, which is attached to a universal cord connected to the control section, and an illumination window attached to the distal end member.

In general, the opposite end portions of one such optical fiber bundle are fixed individually to the control section and the distal end member by means of screws or other mechanical means. A specific arrangement of such fixing means is stated in Japanese Patent Disclosure No. 61-245120, for example. The end portions of the optical fiber bundle are constructed so that simple glass fibers are compacted by means of a bonding agent or the like. Since the mechanical strength of the compacted end portions are very low, reinforcement metal pipes are put individually on the end portions. One of the pipes is fitted in an insertion hole formed in the distal end member, and is fixed to the end member by means of screws.

Conventionally, the aforementioned structure is assembled in the following manner. First, the reinforcement pipes are fitted individually on the end portions of the optical fiber bundle, outside the endoscope. Then, the fiber bundle is passed through the insertion section between the control section and the distal end member. Thereafter, the reinforcement metal pipes at the opposite end portions are fixed individually to the control section and the distal end member.

According to the assembling method described above, however, the optical fiber bundle is previously fitted with the reinforcement pipes, on its end portions, before it is passed through the insertion section. Accordingly, the diameter of the end portions to be inserted is so large that the fiber bundle cannot be easily passed. More specifically, the insertion section of the endoscope is a bendable structure including a bending portion, which is composed of a number of tubular segments rockably coupled to one another. The bending portion houses optical fiber bundles, including an image guide, light guide, etc., forceps channel, gas/liquid feed tube and the like. Accordingly, the bending portion hardly has any inside space through which the optical fiber bundles are to be passed. When an optical fiber bundle with a thick reinforcement metal pipe thereon is passed through the bending portion, therefore, the pipe tends to touch the forceps channel, gas/liquid feed tube, etc. Thus, if the metal pipe is forced into the bending portion, the touched elements may possibly be damaged.

If the metal pipe on the end portion of the optical fiber bundle is reduced in size, therefore, its wall-thickness is also reduced. Thereupon, the mechanical strength of the metal pipe is lowered, so that the pipe may possibly be deformed when it is fixed by means of the screws. If the metal pipe is deformed, then the end portion of the optical fiber bundle will be distorted.

Thus, there is a demand for the development of an improved assembling method for an endoscope in which the optical fiber bundle can be easily passed through the bending portion, and the metal pipes can be fitted on the end portions of the fiber bundle without the consideration of their outside diameter.

SUMMARY OF THE INVENTION

The object of the present invention is to provide an assembling method for an endoscope in which a thick-walled reinforcement pipe with high mechanical strength can be mounted.

The above object of the invention is achieved by the following assembling method for a endoscope. A reinforcement pipe is not on an end portion of an optical fiber bundle when the fiber bundle is passed through an insertion section of the endoscope. In other words, the metal pipe is fitted on the end portion only after the fiber bundle is inserted into the insertion section.

According to the present invention, no reinforcement pipe is on the end portion of the optical fiber bundle when the fiber bundle is passed through the insertion section, so that the end portion to be inserted has a small diameter. Therefore, an insertion space for the fiber bundle, in a flexible tube in which a forceps channel, gas/liquid feed tube, etc. are inserted, can be narrowed. Also, the fiber bundle can be passed with ease. Accordingly, the channel and feed tube in the flexible tube cannot be damaged. Since the reinforcement pipe is put on the end portion of the optical fiber bundle only after the fiber bundle is passed through the insertion section, moreover, the pipe can be increased in outside diameter. Thus, the pipe can have a substantial wall-thickness, so that its mechanical strength is improved. Consequently, the reinforcement pipe cannot be deformed, so that the end portion of the optical fiber bundle can be protected against distortion.

BRIEF DESCRIPTION OF THE DRAWINGS

FIG. 6 is a side view, partially in section, showing a junction of a light guide according to a second embodiment of the invention;

FIG. 7 is an exploded sectional view showing a construction of an insertion section of an endoscope according to third embodiment of the invention; and FIG. 8 is a cross-sectional view taken along line VIII—VIII of FIG. 7.

DETAILED DESCRIPTION OF THE PREFERRED EMBODIMENTS

Figure 1:
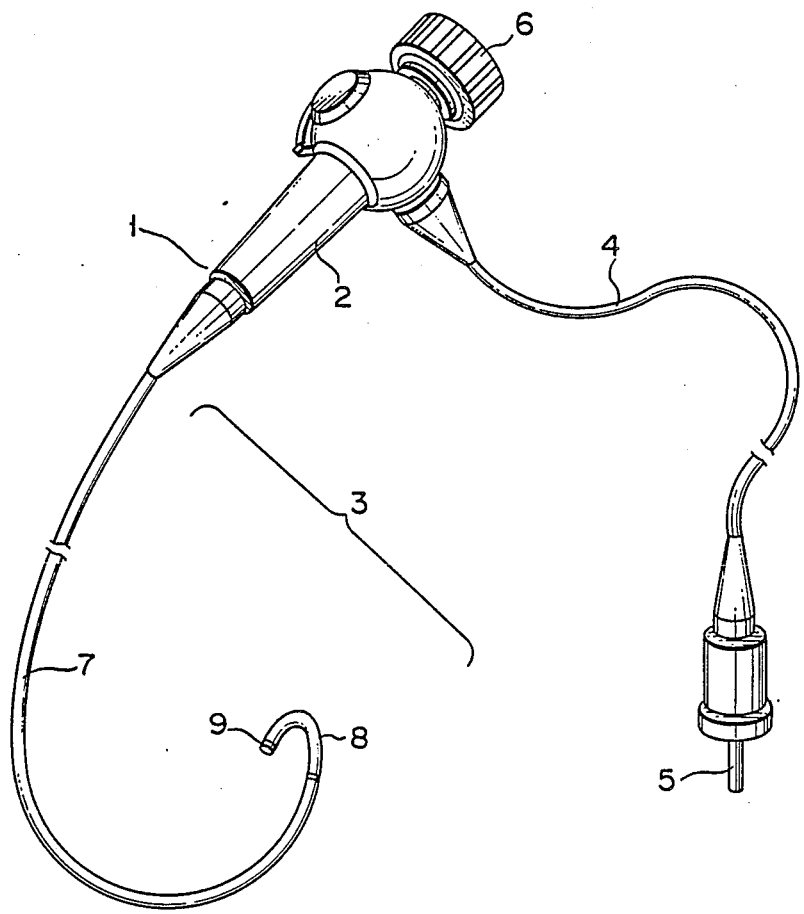
FIG. 1 is a perspective view showing an outline of an endoscope according to a first embodiment of the present invention.

Preferred embodiments of the endoscope according to the present invention will now be described in detail with reference to the accompanying drawings.

FIGS. 1 to 5 show a first embodiment of the present invention. Endoscope 1 shown in FIG. 1 comprises insertion section 3 and control section 2 connected to the proximal end portion of section 3. Insertion section 3 includes flexible tube portion 7, bending portion 8, and distal end member 9. Universal cord 4 is connected to control section 2, and light source connector 5 is provided at the distal end of cord 4. Further, control section 2 is provided with eyepiece portion 6.

Figure 2:
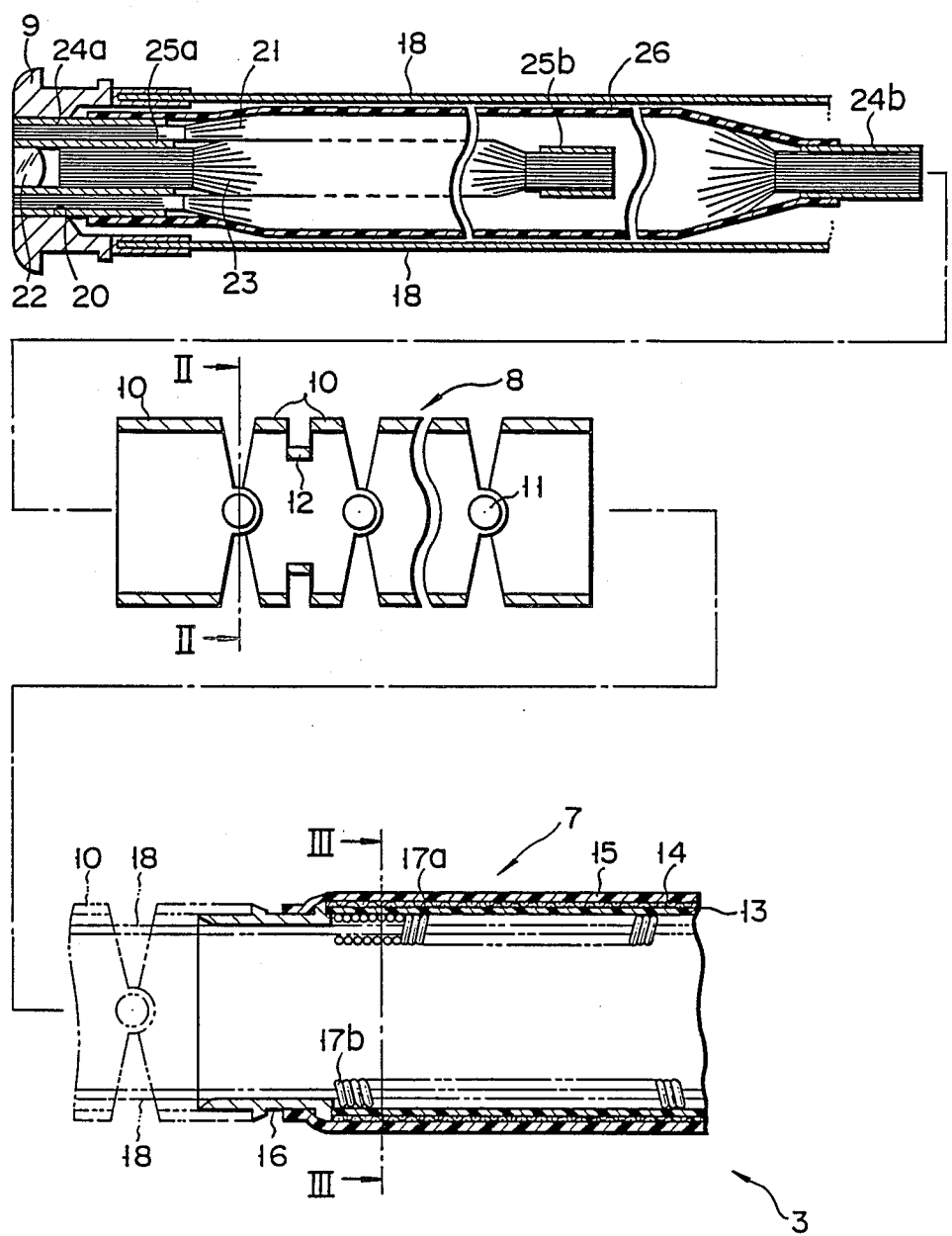
FIG. 2 is a longitudinal sectional view schematically showing an insertion section of the endoscope of FIG. 1.
Figure 3:
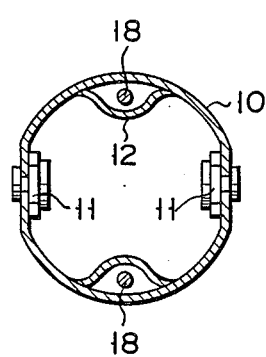
FIG. 3 is a cross-sectional view taken along line II—II of FIG. 2.
Figure 4:
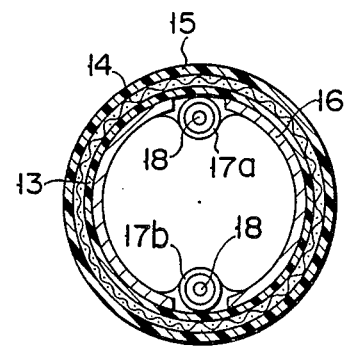
FIG. 4 is a cross-sectional view taken along line III—III of FIG. 2.

Referring now to FIG. 2, insertion section 3 will be described in detail. Bending tube portion 8 is coupled to distal end member 9 of section 3. It includes a plurality of ring-shaped tubular segments 10 which are arranged axially in a line. Each two adjacent segments 10 are linked together for vertical bending by means of shaft 11. These tubular segments 10 are covered by a sheathing tube or mesh tube (not shown). Each segment 10 has constricted portion 12.

Flexible tube portion 7 is connected to bending tube portion 8. It is composed of flexible tube 13, braided tube 14 covering the outer peripheral surface of tube 13, and sheathing 15. The distal end portion of flexible tube portion 7 is connected to bending portion 8 by means of connecting pipe 16, while its proximal end portion is connected to control section 2. Coil-shaped wire guides 17a and 17b are attached to the inner surface of flexible tube 13. Wire 18 is passed through each of guides 17a and 17b.

Various elements are passed through the insertion section constructed in this manner. They include channels, gas/liquid suction pipe, etc. Passed through the channels are medical instruments, such as an image guide, light guide, forceps, catheter, and/or high-frequency therapeutic devices. In connection with this embodiment, a detailed description of these elements is omitted.

Annular illumination window 20 opens to the distal end face of distal end member 9. Light guide 21 for illumination is disposed in window 20. Objective lens 22 is provided at the central part of the distal end face of distal end member 9. Image guide 23 is connected to lens 22. Each of guides 21 and 23 is in the form of a bundle of optical fibers. At both ends of each guide, simple fibers of quartz or the like are compacted by means of a bonding agent. Mouthpieces 24a, 24b, 25a and 25b, each formed of a thin-walled metal tube, are fixedly fitted on the respective end portions of guides 21 and 23.

The outer peripheral surface of light guide 21 is covered by sheathing tube 26 so as not to be directly in contact with tubular segments 10 and the like.

The respective other ends of guides 21 and 23 are guided through insertion section 3 to control section 2. Light guide 21 is connected to connector 5 which is coupled to universal cord 4. Image guide 23 is connected to eyepiece portion 6.

Figure 5:
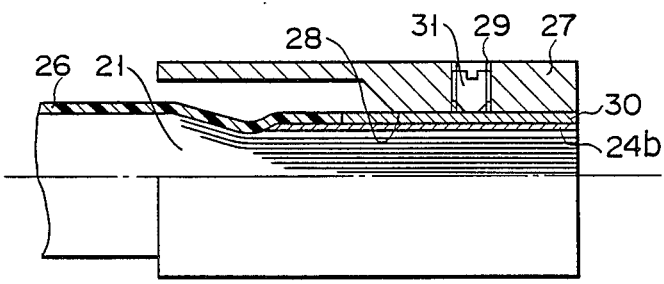
FIG. 5 is a side view, partially in section, showing a junction of a light guide.

FIG. 5 shows connector member 27 in which light guide 21 is connected to light source connector 5. Connector member 27 has insertion hole 28 and tapped hole 29 extending at right angles to hole 28. At the other end of light guide 21, reinforcement pipe 30, formed of e.g. metal, is put on mouthpiece 24b on the light guide, and is bonded to the outer peripheral surface of mouthpiece 24b. Pipe 30 is fitted in insertion hole 28. Screw 31 is screwed in tapped hole 29, thereby immovably fixing the reinforcement pipe.

Image guide 23 is connected to eyepiece portion 6 by means of a connection structure (not shown) similar to the one for light guide 21.

A plurality of operating wires 18 are coupled to distal end member 9. Wires 18 are connected to a pulley of a control knob at control section 2 through constricted portions 12 of tubular segments 10 and their corresponding coil-shaped wire guides 17a, 17b mounted on flexible tube portion 7. Bending portion 8 can be bent by rotating the control knob.

In endoscope 1 with the aforementioned construction, light guide 21 and image guide 23 are assembled in the following manner.

Before guides 21 and 23 are coupled to distal end member 9, they are first assembled together. In doing this, the opposite end portions of the individual fibers of guide 21 are compacted by means of the bonding agent, and mouthpieces 25a and 25b, each in the form of a thin-walled metal tube, are fixedly fitted individually onto the opposite end portions of guide 21. Guide 23 is enclosed by the individual fibers of guide 21. One end of guide 21 is compacted by means of the bonding agent in a manner such that those portions of their fibers which surround mouthpiece 25a attached to one end of guide 23 have equal lengths, and is connectedly fitted with mouthpiece 24a. The other end of guide 21 is also compacted by means of the bonding agent and connectedly fitted with mouthpiece 24b.

In this state, objective lens 22 is attached to mouthpiece 25a on guide 23, and the outer peripheral surface of guide 21 is covered by means of sheathing tube 26. Since guide 21 is much longer than guide 23, the other end of guide 23 on the side of mouthpiece 25b is buried among the fibers of guide 21.

Mouthpiece 24a, which is attached to the one end of guide 21, is fitted into illumination window 20 of distal end member 9, and guides 21 and 23, previously assembled in the aforementioned manner, are fixed by means of the bonding agent. Thus, the respective first ends of guides 21 and 23 are coupled to member 9.

Subsequently, the other ends of guides 21 and 23 are inserted into insertion section 3. Since mouthpiece 25b at the other end of guide 23 is buried among the fibers of guide 21, mouthpiece 24b at the other end of guide 21 is fitted into insertion section 3. Thus, mouthpiece 24b is passed through bending portion 8 and flexible tube portion 7 shown in FIG. 2.

It is essential that the other end of guide 21 is passed through bending portion 8 and flexible tube portion 7 in a manner such that guide 21 is not fitted with metal pipe 30. After the other end of guide 21 is passed through portions 8 and 7 in this manner, the other end of guide 23 is drawn out from among the fibers of guide 21. Thus, that portion of sheathing tube 26 corresponding to the other end of guide 23 is torn to form an opening. The other end of guide 23 is drawn out through this opening. By doing this, the other end of guide 23 is separated from the other end of guide 21.

Then, the respective other ends of guides 21 and 23 are inserted into control section 2. The other end of guide 23 is connected to eyepiece portion 6, while connected to connector 5 is the other end of guide 21, which extends from control section 2 and serves as universal cord 4.

In connecting the other end of guide 21 to connector 5, pipe 30 is fitted on mouthpiece 24b on the other end of guide 21, which extends from control section 2, and is then fixed by means of the bonding agent. Then, pipe 30 is fitted into insertion hole 28 in connector member 27, and screw 31 is screwed into tapped hole 29 to fix the pipe.

In the first embodiment described above, guides 21 and 23 are integrally formed in advance. If the second ends of guides 21 and 23 are inserted into insertion section 3 after their first ends are bonded to distal end member 9, only one guide is practically passed through section 3, since the other end of guide 23 is buried among the fibers of guide 21. Thus, the insertion work can be achieved by only one operation, and the operating efficiency is improved. Since the other end of guide 23 is buried among the fibers of guide 21, moreover, guide 23 cannot be in contact with tubular segments 10 and the like, and therefore, cannot be damaged. Accordingly, guide 23 does not require use of any special sheathing tube, so that the number of components used in the endoscope can be minimized. Since guide 21 is covered by sheathing tube 26, furthermore, it cannot be damaged by touching tubular segments 10.

Thus, the other end of guide 21, without metal pipe 30 (FIG. 5) thereon, can be easily passed through bending portion 8 and flexible tube portion 7. Without the rigid metal pipe, moreover, guide 21 cannot touch the forceps channel, gas/liquid feed tube, or other elements in the insertion section as its other end is passed.

Reinforcement pipe 30 shown in FIG. 5 is attached to the other end of guide 21 only after the guide end is passed through bending portion 8 and flexible tube portion 7. Therefore, pipe 30 can have a relatively large outside diameter and, hence, high mechanical strength, so that it cannot be deformed by the fixing work using screw 31. Thus, the other end guide 21 cannot be distorted.

Although pipe 30 is formed of metal in the aforementioned embodiment, it may alternatively be formed of synthetic resins. If it is compressed by screw 31, the plastic reinforcement pipe absorbs the compressive force by its own elasticity, so that the optical fiber bundle can be prevented from being distorted.

FIG. 6 shows a second embodiment of the present invention. In this embodiment, reinforcement pipe 30 is fitted on mouthpiece 24b at the other end of guide 21 by means of elastic bonding agent 35, such as epoxy or silicone resin. If pipe 30 is thin-walled and is deformed by the compressive force of screw 31, the compressive force is absorbed by bonding agent 35, so that the optical fiber bundle cannot be distorted. In this case, bonding agent 35 may be loaded into only both end portions of pipe 30, without filling up the whole interior of the pipe.

FIGS. 7 and 8 show a third embodiment of the present invention. In this embodiment. flexible tube 40 constitutes an insertion section of an endoscope. Tube 40 is formed of a flexible resin, such as polyurethane, polyvinyl chloride, or PTFE, which may be generally used for celomic catheters. Flexible tube 40 is in the form of a so-called multi-lumen tube, in which a plurality of axial bores 41 are formed independently of one another. Bores 41 are adapted to receive optical fiber bundles, operating wires, forceps channel, etc. One of the optical fiber bundles passed through flexible tube 40, e.g., image guide 42, is a semi-flexible structure which is obtained by entirely coating a bundle of glass fibers, such as quartz fibers, with silicone resin. Objective lens 43 is bonded to the distal end of guide 42 by means of body tube 44. The outside diameter of tube 44 is greater than that of guide 42.

Bore 41 of flexible tube 40, through guide 42 is passed, has a diameter equal to the outside diameter of guide 42. Also, the inside diameter of inlet portion 45 at an end of bore 41 is substantially equal to the outside diameter of body tube 44.

In the arrangement described above, an end portion of guide 42 (on the opposite side to body tube 44) is inserted into flexible tube 40 through inlet portion 45 at the end thereof, and is drawn out from the other end of bore 41. Thereafter, reinforcement pipe 30, formed of metal or resin, is put on the end portion of guide 42.

Also in this embodiment, pipe 30 is fitted on the end portion of guide 42 which is passed through bore 41 of flexible tube 40. As in the case of the first embodiment, therefore, the outside diameter of pipe 30 can be enlarged to increase its mechanical strength. Thus, the diameter of image guide 42 can be minimized, so that bore 41 can be narrowed, that is, flexible tube 40 can be thinned.

The optical fiber bundle may be inserted not only from distal end member 9 toward control section 2, but also from section 2 toward member 9.

According to the present invention described above, the optical fiber bundle is passed through the insertion section before it is fitted with the reinforcement pipe at its end portion. Accordingly, the fiber bundle is relatively thin, so that an insertion space for the fiber bundle, in the flexible tube through which the forceps channel, gas/liquid feed tube, and other channels or tubes are passed, can be narrowed. Thus, the insertion work for the fiber bundle is facilitated, and the channels and tubes cannot be damaged thereby. Since the pipe is put on the end portion of the optical fiber bundle only after the fiber bundle is passed through the insertion section, moreover, the pipe can be increased both in outside diameter and in wall-thickness. Therefore, the reinforcement pipe can enjoy too high a mechanical strength to be deformed. Thus, the end portion of the optical fiber bundle can be protected against distortion.

What is claimed is:

1. A method for assembling optical fiber bundles in an endoscope, comprising:
    an insertion step of passing at least one optical fiber bundle through a flexible tube constituting an insertion section of the endoscope;
    a fitting step of fitting a reinforcement pipe member in at least one end portion of the optical fiber bundle passed through the flexible tube; and
    a coupling step of coupling the opposite end portions of the optical fiber bundle, on which the reinforcement pipe member is fitted, individually to a control section and a distal end member of the endoscope.

2. A method according to claim 1, wherein said optical fiber bundle is composed of an image guide and a light guide, and said insertion step includes a compacting step of compacting both end portions of the image guide and the light guide by means of a bonding agent and fitting mouthpieces individually on the end portions of the guides.

3. A method according to claim 1, wherein said optical fiber bundle is composed of an image guide and a light guide, and said insertion step includes a covering step of covering the image guide with the light guide.

4. A method according to claim 1, wherein said optical fiber bundle is composed of an image guide and a light guide, and said insertion step includes a drawing step of tearing the light guide and drawing out the image guide from the light guide.

5. A method according to claim 1, wherein said reinforcement pipe member is fixed by means of a bonding agent when said pipe member is fitted on the end portion of the optical fiber bundle in said fitting step.

6. A method according to claim 5, wherein said bonding agent is formed of an elastic resin, such as epoxy resin or silicone resin.

7. A method according to claim 1, wherein said reinforcement member is formed of metal.

8. A method according to claim 1, wherein said reinforcement member is formed of a synthetic resin.

9. A method according to claim 1, wherein said flexible tube is formed of a flexible resin, such as polyurethane, polyvinyl chloride, or PTFE.

10. A method according to claim 1, wherein said flexible tube is a multi-lumen tube.

* * * * *